(12) United States Patent
Wurziger et al.

(10) Patent No.: US 7,179,925 B2
(45) Date of Patent: Feb. 20, 2007

(54) METHOD FOR REDUCING ORGANIC COMPOUNDS IN MICROREACTOR BY MEANS OF HYDRIDES AND/OR THE DERIVATIVES THEREOF

(75) Inventors: Hanns Wurziger, Darmstadt (DE); Guido Pieper, Mannheim (DE); Norbert Schwesinger, Ilmenau (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/239,393

(22) PCT Filed: Mar. 1, 2001

(86) PCT No.: PCT/EP01/02302

§ 371 (c)(1),
(2), (4) Date: Jan. 8, 2003

(87) PCT Pub. No.: WO01/70649

PCT Pub. Date: Sep. 27, 2001

(65) Prior Publication Data

US 2004/0225157 A1    Nov. 11, 2004

(30) Foreign Application Priority Data

Mar. 23, 2000 (DE) ............... 100 14 298

(51) Int. Cl.
*C07D 233/54* (2006.01)
(52) U.S. Cl. .................................. 548/341.1
(58) Field of Classification Search ............. 548/341.1
See application file for complete search history.

(56) References Cited

U.S. PATENT DOCUMENTS 5,091,595 A * 2/1992 Choi ..................... 568/814

OTHER PUBLICATIONS

Jacquot et al., 2003, CAS:139:149422.*
Nizzola et al., 1992, CAS:117:233704.*
Richter et al., 1999, CAS:130:353925.*

* cited by examiner

*Primary Examiner*—Joseph K. McKane
*Assistant Examiner*—Robert Shiao
(74) *Attorney, Agent, or Firm*—Millen, White, Zelano, Branigan, P.C.

(57) ABSTRACT

The present invention relates to a process for the reduction of aliphatic, aromatic or heterocyclic organic compounds by means of hydrides and/or derivatives thereof.

34 Claims, No Drawings

METHOD FOR REDUCING ORGANIC COMPOUNDS IN MICROREACTOR BY MEANS OF HYDRIDES AND/OR THE DERIVATIVES THEREOF

This application is a 371 of PCT/EP 01/02302 filed on Mar. 1, 2001.

The present invention relates to a process for the reduction of aliphatic, aromatic or heterocyclic organic compounds by means of hydrides and/or derivatives thereof.

The reduction of suitable aliphatic, aromatic or heterocyclic organic compounds by means of hydrides and/or derivatives thereof is a process which is carried out very frequently in the chemical industry and whose considerable importance is also reflected in numerous publications on this subject.

However, the performance of reductions by means of hydrides and/or derivatives thereof on an industrial scale is accompanied by safety problems and dangers. Firstly, use is frequently made of relatively large amounts of highly toxic chemical substances, which in themselves already represent a considerable risk to people and the environment, and secondly the reaction conditions can in many cases only be controlled well with considerable effort. Furthermore, the achievement and maintenance of protective-gas conditions is often very complex in industrial-scale reductions of this type.

The object of the present invention is therefore to provide a process for the reduction of aliphatic, aromatic or heterocyclic organic compounds by means of hydrides and/or derivatives thereof which avoids the above-mentioned disadvantages. In particular, It should be possible to carry out this process in a simple, reproducible manner with increased safety for humans and the environment and with good yields, the reaction conditions should be very easy to control, and the protective-gas conditions necessary for carrying out the reaction should be achievable without major technical effort.

This object is achieved, surprisingly, by the process according to the invention for the reduction of aliphatic, aromatic or heterocyclic organic compounds by means of hydrides and/or derivatives thereof, in which at least one organic compound in liquid or dissolved form is mixed with at least one hydride and/or derivative thereof in liquid or dissolved form in at least one microreactor and reacted for a residence time, and the reduced organic compound is, if desired, isolated from the reaction mixture.

Advantage embodiments of the process according to the invention are claimed in the sub-claims.

In accordance with the invention, an aliphatic, aromatic or heterocyclic organic compound or a mixture of at least two of these compounds is reduced by the claimed process. Preferably, only one aliphatic, aromatic or heterocyclic organic compound is employed in the process according to the invention.

For the purposes of the invention, a microreactor is a reactor having a volume of $\leq 1000$ µl in which the liquids and/or solutions are intimately mixed at least once. The volume of the reactor is preferably $\leq 100$ µl, particularly preferably $\leq 50$ µl.

The microreactor is preferably made from thin silicon structures connected to one another.

The microreactor is preferably a miniaturised flow reactor, particularly preferably a static micromixer. The microreactor is very particularly preferably a static micromixer as described in the patent application having the international publication number WO 96/30113, which is incorporated herein by way of reference and is regarded as part of the disclosure.

A microreactor of this type has small channels in which liquids and/or chemical compounds in the form of solutions are mixed with one another by means of the kinetic energy of the flowing liquids and/or solutions.

The channels of the microreactor preferably have a diameter of from 10 to 1000 µm, particularly preferably from 20 to 800 µm and very particularly preferably from 30 to 400 µm.

The liquids and/or solutions are preferably pumped into the microreactor in such a way that they flow through the latter at a flow rate of from 0.01 µl/min to 100 ml/min, particularly preferably from 1 µl/min to 1 ml/min.

In accordance with the invention, the microreactor is preferably heatable.

In accordance with the invention, the microreactor is preferably connected via an outlet to at least one residence zone, preferably a capillary, particularly preferably a heatable capillary. After mixing in the microreactor, the liquids and/or solutions are fed into this residence zone or capillary in order to extend their residence time.

For the purposes of the invention, the residence time is the time between mixing of the starting materials and work-up of the resultant reaction solution for analysis or isolation of the desired product(s).

The residence time necessary in the process according to the invention depends on various parameters, such as, for example, the temperature or reactivity of the starting materials. It is possible for the person skilled in the art to match the residence time to these various parameters and thus to achieve an optimum course of the reaction.

The residence time of the reaction solution in the system used comprising at least one microreactor and, if desired, a residence zone can be adjusted through the choice of the flow rate of the liquids and/or solutions employed.

The reaction mixture is likewise preferably passed through two or more microreactors connected in series. This achieves an extension of the residence time, even at an increased flow rate, and the reduction reaction components employed are reacted in such a way that an optimum product yield of the desired reduced organic compound(s) is achieved.

In a further preferred embodiment, the reaction mixture is passed through two or more microreactors arranged in parallel in order to increase the throughput.

In another preferred embodiment of the process according to the invention, the number and arrangement of the channels in one or more microreactor(s) are varied in such a way that the residence time is extended, likewise resulting in an optimum yield of the desired reduced organic compound(s) at the same time as an increased flow rate.

The residence time of the reaction solution in the microreactor, where appropriate in the microreactor and the residence zone, is preferably $\leq 15$ hours, particularly preferably $\leq 3$ hours, very particularly preferably $\leq 1$ hour.

The process according to the invention can be carried out in a very broad temperature range, which is essentially restricted by the heat resistance of the materials employed for the construction of the microreactor, any residence zone and further constituents, such as, for example, connections and seals, and by the physical properties of the solutions and/or liquids employed. The process according to the invention is preferably carried out at a temperature of from −100 to +250° C., particularly preferably from −78 to +150° C. and very particularly preferably from 0 to +40° C.

The process according to the invention can be carried out either continuously or batchwise. It is preferably carried out continuously.

For carrying out the process according to the invention for the reduction of aliphatic, aromatic or heterocyclic organic compounds by means of hydrides and/or derivatives thereof, it is necessary for the reduction reaction to be carried out as far as possible in the homogeneous liquid phase containing no or only very small solid particles, since otherwise the channels present in the microreactors become blocked.

The course of the reduction reaction in the process according to the invention can be followed using various analytical methods known to the person skilled in the art and if necessary regulated. The course of the reaction is preferably followed by chromatography, particularly preferably by gas chromatography and/or high-pressure liquid chromatography, and if necessary regulated. In this case, control of the reaction is significantly improved in the process according to the invention compared with known processes.

After the reaction, the reduced organic compounds are isolated if desired. The reduced product(s) is (are) preferably isolated from the reaction mixture after work-up of the reaction mixture, for example by acidification using hydrochloric acid, if desired neutralisation and subsequent extraction with a suitable solvent. The extraction is particularly preferably carried out with an organic solvent.

Aliphatic, aromatic or heterocyclic organic compounds which can be employed in the process according to the invention are all aliphatic, aromatic or heterocyclic organic compounds which are known to the person skilled in the art as substrates of reductions by means of hydrides and/or derivatives thereof.

Preferred aliphatic, aromatic or heterocyclic organic compounds are aliphatic, aromatic or heterocyclic carbonyl compounds, such as aldehydes and ketones, carboxylic acids, carboxylic acid halides, carboxylic acid esters, corresponding thio or seleno analogues of the above-mentioned compounds, nitrites, halides or azides.

Aliphatic carbonyl compounds, carboxylic acids, carboxylic acid halides, carboxylic acid esters, corresponding thio or seleno analogues of the above-mentioned compounds, nitrites, halides or azides which can be employed are all aliphatic compounds from the above-mentioned classes of substance which are known to the person skilled in the art and which are suitable as substrate for reductions by means of hydrides and/or derivatives thereof. Straight-chain, branched, saturated and unsaturated compounds are also included here.

Aromatic carbonyl compounds, carboxylic acids, carboxylic acid halides, carboxylic acid esters, corresponding thio or seleno analogues of the above-mentioned compounds, nitrites, halides or azides which can be employed are all aromatic compounds from the above-mentioned classes of substance which are known to the person skilled in the art and which are suitable as substrate for reductions by means of hydrides and/or derivatives thereof. For the purposes of the invention, this also includes compounds and/or derivatives which have a monocyclic and/or polycyclic homoaromatic basic structure or a corresponding moiety, for example in the form of substituents.

Heterocyclic carbonyl compounds, carboxylic acids, carboxylic acid halides, carboxylic acid esters, corresponding thio or seleno analogues of the above-mentioned compounds, nitrites, halides or azides which can be employed are all heterocyclic compounds from the above-mentioned classes of substance which are known to the person skilled in the art and which are suitable as substrate for reductions by means of hydrides and/or derivatives thereof and which contain at least one heteroatom. For the purposes of the invention, heterocyclic compounds also include heterocyclic compounds and/or derivatives thereof which have at least one monocyclic and/or polycyclic heterocyclic basic structure or a corresponding moiety, for example in the form of substituents. The term "heterocyclic" here also includes saturated, unsaturated and heteroaromatic compounds. Heterocyclic basic structures or moieties particularly preferably include at least one oxygen, nitrogen or sulfur atom.

Reducing agents which can be employed in the process according to the invention are all hydrides and/or derivatives thereof which are known to the person skilled in the art and are suitable for reductions of aliphatic, aromatic or heterocyclic organic compounds. The hydride or derivative thereof used is preferably at least one compound selected from boron hydrides, aluminium hydrides, tin hydrides and silicon hydrides, derivatives thereof and mixtures of these reducing agents. Preferably, in each case only one hydride or derivative is employed as reducing agent in the process according to the invention.

For the purposes of the invention, a derivative of a hydride is a structurally analogous compound in which at least one hydrogen atom has been replaced by a radical other than hydrogen, but at least one hydrogen atom is still present.

The boron hydride or derivative thereof used is preferably lithium borohydride, sodium borohydride, potassium borohydride, rubidinium borohydride, caesium borohydride, zinc borohydride, calcium borohydride, copper borohydride, tetraalkylammonium borohydride, trialkylphosphonium borohydride or triarylphosphonium borohydride, or alkyl, aryl, alkoxy, aryloxy, acyloxy, cyano or heteroaryl derivatives of the borohydrides or a mixture of the above-mentioned compounds. The borohydride or derivative thereof used is likewise preferably a borane, in particular diborane, or alkyl, aryl, alkoxy, aryloxy, acyloxy or heteroaryl derivatives of the boranes, complexes of the boranes or of the above derivatives with amines, phosphines, ethers or sulfides as ligands, where the ligands may in each case be identical or different, or a mixture of the above-mentioned compounds. The aluminium hydride or derivative thereof employed is preferably alane ($AlH_3$), complex aluminium hydrides, in particular lithium aluminium hydride, sodium aluminium hydride, potassium aluminium hydride, or alkyl, aryl, alkoxy, aryloxy or acyloxy derivatives of alane or of the aluminium hydrides, for example Na bis(2-methoxyethoxy) aluminium hydride or diisobutylaluminium hydride. Preference is likewise given to complexes of alane, of the aluminium hydrides or of the above derivatives with amines, phosphines, ethers or sulfides as ligands, where the ligands may in each case be identical or different, or a mixture of the above-mentioned compounds. Preferred silicon hydrides or derivatives thereof include silanes, in particular monosilane, and alkyl, aryl, alkoxy, aryloxy, acyloxy, cyano or heteroaryl derivatives of the silanes, or a mixture of the above-mentioned compounds. Examples of preferred tin hydrides or derivatives thereof include stannanes, in particular monostannane, and alkyl, aryl, alkoxy, aryloxy, acyloxy, cyano or heteroaryl derivatives of the stannanes, or a mixture of the above-mentioned compounds.

Alkenes and alkynes are capable of insertion into the B-H bonds of boranes. Hydrolysis or peroxohydrolysis of the organoboranes formed in these hydroboration reactions results in hydrocarbons or alcohols. It must therefore, where appropriate, be taken into account that these hydroborations can likewise occur in the case of unsaturated compounds which are to be reduced in accordance with the invention if boranes and/or derivatives of the boranes are employed as reducing agent.

Suitable substituents of the hydride derivatives are all alkyl, aryl, alkoxy, aryloxy, acyloxy or heteroaryl substituents which are known to the person skilled in the art and which can be employed in reductions of aliphatic, aromatic or heterocyclic compounds.

In the process according to the invention, the molar ratio of organic compound to hydride and/or derivative thereof employed depends on the reactivity of the organic compounds, hydrides and/or derivatives employed. The hydride and/or derivative thereof is preferably employed in an excess of >1 or in an equimolar amount with respect to the organic compound.

The selectivity of the reaction depends, besides on the concentration of the reagents employed, on a number of further parameters, such as, for example, the temperature, the type of reducing agent used or the residence time. It is possible for the person skilled in the art to match the various parameters to the respective reduction reaction in such a way that the desired reduced product(s) is (are) obtained.

It is essential for the process according to the invention that the organic compounds and reducing agent employed are either themselves liquid or are in dissolved form. If these compounds are not themselves already in liquid form, they must therefore be dissolved in a suitable solvent before the process according to the invention is carried out. Preferred solvents are aromatic solvents, particularly preferably toluene, xylenes, ligroin or phenyl ether, straight-chain, branched or cyclic paraffins, particularly preferably pentane, hexane, heptane, octane, cyclopentane, cyclohexane, cycloheptane or cyclooctane, or straight-chain, branched or cyclic ethers, particularly preferably diethyl ether, methyl tert-butyl ether, tetrahydrofuran or dioxane, or mixtures of these solvents.

In the process according to the invention, the danger to people and the environment due to released chemicals is considerably reduced and thus results in increased safety during handling of hazardous materials. The reduction of aliphatic, aromatic or heterocyclic organic compounds by the process according to the invention furthermore enables better control of the reaction conditions, such as, for example, reaction duration and reaction temperature, than is possible in the conventional processes. The temperature can be selected individually and kept constant in each volume unit of the system. The course of the reaction in the reduction can be regulated very quickly and precisely in the process according to the invention. Protective-gas conditions can be achieved and maintained very easily. The reduced organic products can thus be obtained in very good and reproducible yields.

It is also particularly advantageous that the process according to the invention can be carried out continuously. This makes it faster and less expensive compared with conventional processes, and it is possible to prepare any desired amounts of the reduced organic compounds without major measurement and control effort.

The invention is explained below with reference to an example. This example serves merely to explain the invention and does not restrict the general inventive idea.

EXAMPLES

Reduction of methyl 3-(3-methyl-3H-imidazol-4-yl) acrylate to 3-(3-methyl-3H-imidazol-4-yl)prop-2-en-1-ol The reduction of methyl 3-(3-methyl-3H-imidazol-4-yl) acrylate using diisobutylaluminium hydride (DIBAL-H) was carried out in a static micromixer (Technical University of Ilmenau, Faculty of Machine Construction, Dr.-Ing. Norbert Schwesinger, PO Box 100565, D-98684, Ilmenau) having a physical size of 0.8 mm×0.8 mm×0.6 mm and having a total of 11 mixing stages with a volume of 0.125 µl each. The total pressure loss was about 1000 Pa.

The static micromixer was connected via an outlet and an Omnifit medium-pressure HPLC connector (Omnifit, Great Britain) to a Teflon capillary having an internal diameter of 0.49 mm and a length of 1.0 m. The reaction was carried out at room temperature.

A 2 ml disposable injection syringe was filled with a solution of 0.84 g (50 mmol) of methyl 3-(3-methyl-3H-imidazol-4-yl)acrylate and 10 ml of toluene, and a further 2 ml syringe was filled with a 20% solution of diisobutylaluminium hydride (DIBAL-H) in hexane. The contents of the two syringes were subsequently transferred into the static micromixer by means of a metering pump (Harvard Apparatus Inc., Pump 22, South Natick, Mass., USA). Before performance of the reaction, the experimental arrangement was calibrated with respect to the dependence of the residence time on the pump flow rate. The residence time was set to 30, 15, 7.5 or 3.75 minutes. The reactions were followed with the aid of a Hewlett-Packard GC-MS instrument or a Merck Hitachi LaChrom HPLC instrument.

The resultant reaction mixture was acidified using 1 N HCl and extracted with ethyl acetate. The organic extract was subsequently dried over magnesium sulfate and freed from solvent under reduced pressure.

The invention claimed is:

1. A process for the reduction of an aliphatic, aromatic or heterocyclic organic compound by a hydride and/or a derivative thereof, comprising reacting at least one aliphatic, aromatic or heterocyclic organic compound in liquid or dissolved form with at least one hydride derivative or borohydride derivative, in a microreactor for a residence time, and optionally isolating the reduced organic compound from the reaction mixture.

2. A process according to claim 1, wherein the microreactor is a miniaturised flow reactor.

3. A process according to claim 1, wherein the microreactor is a static micromixer.

4. A process according to claim 1, wherein the microreactor is connected via an outlet to a capillary.

5. A process according to claim 1, wherein the volume of the microreactor is $\leq 100$ µl.

6. A process according to claim 1, wherein the microreactor is heatable.

7. A process according to claim 1, wherein the microreactor has channels having a diameter of from 10 to 1000 µm.

8. A process according to claim 1, wherein the reaction mixture flows through the microreactor at a flow rate of from 0.01 µl/mm to 100 ml/min.

9. A process according to claim 1, wherein the residence time of the compounds employed in the microreactor or in the microreactor and the capillaries is $\leq 15$ hours.

10. A process according to claim 1, wherein said process is carried out at a temperature of from −100 to +250° C.

11. A process according to claim 1, wherein the course of the reaction is followed by chromatography and optionally regulated.

12. A process according to claim 1, wherein the aliphatic, aromatic or heterocyclic organic compound is a carbonyl compound, a carboxylic acid, a carboxylic acid halide, a carboxylic acid ester, a corresponding thio or seleno analog of the above-mentioned compounds, a nitrite, a halide or an azide.

13. A process according to claim 1, wherein the hydride or a derivative thereof is boron hydride, aluminium hydride, tin hydride, silicon hydride, a derivative thereof or a mixture thereof.

14. A process according to claim 13, wherein the boron hydride or a derivative thereof is lithium borohydride, sodium borohydride, potassium borohydride, rubidium borohydride, caesium borohydride, zinc borohydride, calcium borohydride, copper borohydride, tetraalkyl-ammonium borohydride, trialkylphosphonium borohydride or triarylphosphonium borohydride, or an alkyl, aryl, alkoxy, aryloxy, acyloxy, or cyano of the borohydrides, or a mixture thereof.

15. A process according to claim 13, wherein the borohydride or a derivative thereof is a borane or an alkyl, aryl, alkoxy, aryloxy, or acyloxy of borane, a complex of borane or a complex of the derivatives with, an amine, a phosphine, an ether, or a sulfide, or a mixture thereof.

16. A process according to claim 13, wherein the aluminium hydride is alane ($AlH_3$).

17. A process according to claim 13, wherein the aluminium hydride or a derivative thereof is a complex aluminium hydride, or an alkyl, aryl, alkoxy, aryloxy or acyloxy derivative of the aluminium hydrides, a complex of the aluminium hydrides or a complex of the derivatives with an amine, a phosphine, an ether, or a sulfide, or a mixture thereof.

18. A process according to claim 13, wherein the aluminium hydride derivative is diisobutylaluminium hydride.

19. A process according to claim 17, wherein the complex aluminium hydride is Na bis(2-methoxyethoxy)aluminium hydride.

20. A process according to claim 13, wherein the silicon hydride or a derivative thereof is a silane, or an alkyl, aryl, alkoxy, aryloxy, acyloxy, or cyano of the silane, or a mixture thereof.

21. A process according to claim 13, wherein the tin hydride or a derivative thereof is a stannane, an alkyl, aryl, alkoxy, aryloxy, acyloxy, or cyano of the stannane, or a mixture thereof.

22. A process according to claim 1, wherein the hydride and/or a derivative thereof is employed in a molar excess of >1 or in an equimolar amount with respect to the organic compound.

23. A method as in claim 1, wherein the microreactor is a device for mixing liquids, wherein mixing is effected by the flowing of the liquids through narrow channels, said device comprising:
at least one mixing element having at least one inlet channel and at least one outlet channel, wherein said mixing element is arranged on at least one substrate having planar surface;
at least two microchannels issuing from said inlet channel, said at least two microchannels lying in a same branching plane;
a confluence element being connected by a connection to said microchannels, wherein the connection effects a 90° rotation of the inflow of the liquid relative to said branching plane as the liquid flows from said microchannels to said confluence element;
said at least one outlet channel being connected to said confluence element; and
a covering hermetically sealing the planar surface of said at least one substrate to cover the mixing element.

24. A process according to claim 4, wherein said capillary is a heatable capillary.

25. A process according to claim 5, wherein said volume of the microreactor is $\leq 50$ µl.

26. A process according to claim 7, wherein the microreactor has channels having a diameter of from 30 to 400 µm.

27. A process according to claim 8, wherein said flow rate is from 1 µl/min to 1 ml/min.

28. A process according to claim 9, wherein said residence time is $\leq 1$ hour.

29. A process according to claim 10, wherein said process is carried out at a temperature of from 0 to +40° C.

30. A process according to claim 11, wherein said course of the reaction is followed by gas chromatography.

31. A process according to claim 15, wherein said borohydride is diborane.

32. A process according to claim 17, wherein said aluminium hydride is lithium aluminium hydride, sodium aluminium hydride, or potassium aluminium hydride.

33. A process according to claim 20, wherein said silicon hydride is monosilane.

34. A process according to claim 21, wherein said tin hydride is monostanane.

* * * * *